United States Patent [19]

Pakulis

[11] Patent Number: 4,485,284
[45] Date of Patent: Nov. 27, 1984

[54] APPARATUS AND PROCESS FOR MICROWAVE MOISTURE ANALYSIS

[75] Inventor: Ivars E. Pakulis, Arlington Heights, Ill.

[73] Assignee: Advanced Moisture Technology, Inc., Wauconda, Ill.

[21] Appl. No.: 338,346

[22] Filed: Jan. 11, 1982

[51] Int. Cl.³ .............................................. H05B 9/06
[52] U.S. Cl. ....................... 219/10.55 R; 219/10.55 F; 324/58.5 A; 73/73; 374/14
[58] Field of Search ................. 219/10.55 R, 10.55 A, 219/10.55 M; 324/58.5 A, 58, 58.5 B; 343/18 A; 374/14; 73/73, 76

[56] References Cited

U.S. PATENT DOCUMENTS

| | | | |
|---|---|---|---|
| 2,659,860 | 11/1953 | Breazeale | 324/49 |
| 3,290,598 | 12/1966 | Thomas | 325/67 |
| 3,295,133 | 12/1966 | Emerson et al. | 343/18 |
| 3,460,030 | 8/1969 | Brunton et al. | 324/58.5 |
| 3,499,499 | 10/1967 | Bilbrough | 324/58.5 A |
| 3,501,692 | 3/1970 | Kluck | 324/58.5 A |
| 3,553,573 | 1/1971 | Lundstrom et al. | 324/58.5 A |
| 3,815,019 | 7/1974 | Wiles | 324/58.5 A |
| 3,818,333 | 6/1974 | Walker | 324/58.5 A |
| 4,103,224 | 7/1978 | Taro et al. | 324/58.5 A |
| 4,104,584 | 8/1978 | Miyai et al. | 324/58.5 A |
| 4,131,845 | 12/1978 | Pakulis | 324/58.5 A |
| 4,206,399 | 6/1980 | Fitzky et al. | 324/58.5 B |

OTHER PUBLICATIONS

IEEE Transactions on Industrial Electronics and Control Instrumentation, vol. IECI-23, No. 4, pp. 364–370, Nov. 1976, "*An Improved Microwave Method of Moisture Content Measurement and Control*", Kraszewski & Kulinski.

*Primary Examiner*—C. L. Albritton
*Assistant Examiner*—M. M. Lateef
*Attorney, Agent, or Firm*—Wood, Dalton, Phillips, Mason & Rowe

[57] ABSTRACT

An apparatus and process is disclosed for enabling the measurement of moisture in a sample cell by use of microwave energy. A sample cell of predetermined volume is located within an anechoic chamber and positioned on a weight measuring device to measure the weight of any material in the sample cell. Microwave energy is directed through the material in the sample cell by means of a transmitter and receiver to provide a measurement of the water weight in the sample. A temperature sensor is located to measure the temperature in the cell and the reading is combined with the microwave water weight measurement and the weight of the sample to calculate the percent moisture and the bulk density of the material.

18 Claims, 1 Drawing Figure

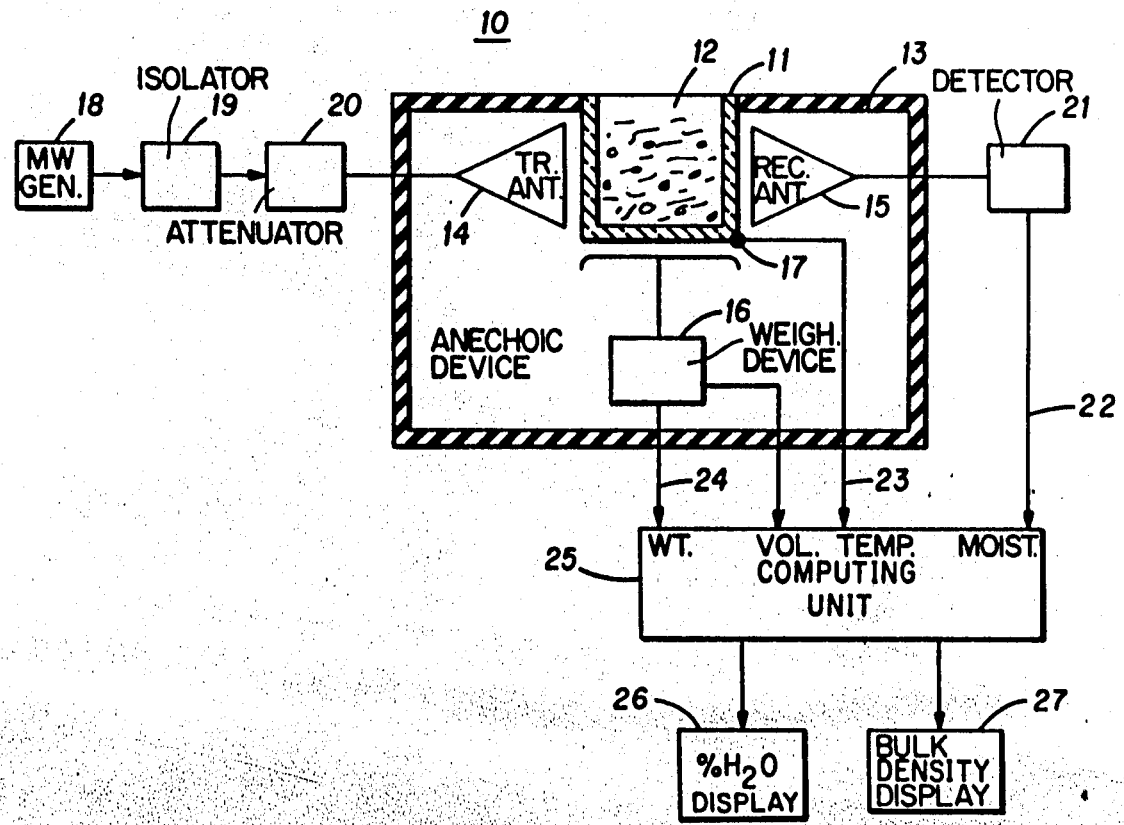

APPARATUS AND PROCESS FOR MICROWAVE MOISTURE ANALYSIS

THE BACKGROUND OF THE INVENTION

The present invention relates to a moisture measuring apparatus and technique and, more specifically, to the use of microwave energy to measure the percent moisture in a predetermined volume.

The use of microwave energy to aid in the determination of moisture content in different materials is well known in the art. In such devices and processes, microwaves are propagated through a particular material and are attenuated by an amount dependent on the quantity of moisture in the product. At the same time, gamma or other radiation is directed through the material and also attenuated depending upon the density of the material. With an appropriate combination of the two measurements of microwave and other radiation, a reading approximating the percent moisture of the sample can be obtained. Naturally, the accuracy of any reading will be dependent upon the accuracy of detecting the attenuation of the microwave and other radiation signals transmitted through the sample material.

Apparatus employing the above techniques are disclosed, for example, in U.S. Pat. Nos. 3,460,030 and 4,131,845. In the exampled instances, the measurements are made in connection with material moving in a chute or trough to enable a continuous measurement of the percent moisture content in processed material. Although such devices have enabled the calculation of an approximate percentage of moisture content, they have been somewhat complex and not suitable for making inexpensive measurements of discrete quantities of sampled material.

In U.S. Pat. No. 3,499,499, rather than determine the percent moisture content of a material, microwaves are used to determine the water weight so that adjustments in the dry weight of a material can be made. This technique enables the compensation for moisture in material, but does not provide for a direct reading of the percent moisture contained in any given sample.

The device in U.S. Pat. No. 3,499,499 also lacks two features which would be needed for accurate moisture analysis with microwave methods. It is well known in the art that microwave characteristics of water are affected by temperature. No means of measuring or compensating for temperature effects are provided. In addition, repeatability and accuracy of moisture measurement is greatly enhanced if microwave propagation in the measurement zone is optimized. U.S. Pat. No. 4,131,845 is particularly concerned with providing microwave absorbent material on the inside of the chute sensor to adjust microwave characteristics of the sensor for best measurement accuracy.

In still other instances, the percent moisture content in a given sample has been calculated by an evaporative technique. In those instances, the sample is first weighed and then subjected to heat to cause the evaporation of moisture in the sample. The sample is then weighed again and the difference in material weight preceding and following the drying enables the calculation of the percent moisture content. Such processes, however, normally require a long drying time to prevent the possibility of burning the material. In addition, in order to decrease such drying time, the samples are often ground or otherwise altered and the heat generated during such alteration varies the original moisture content resulting in an inaccurate final reading. Finally, during the drying process, other volatiles in the material may be evaporated, thereby resulting in an inaccurate final moisture reading.

In an attempt to increase the speed of the above drying technique, some techniques have employed microwave radiation to perform the drying process. While this technique improves the drying time, and works satisfactorily with relatively high moisture materials, the effectiveness of the microwave drying significantly decreases as the moisture content of the material decreases. This condition is caused by the decrease in water molecules with which the microwave energy may interact at the lower moisture contents. Restrictions on the use of particular microwave frequencies for drying also prevent the use of optimum frequency with the water molecule. This, likewise, reduces the sensitivity to materials with low moisture content.

The present invention has been developed to overcome the specific shortcomings of the above known and similar techniques and to provide for microwave measurement of percent moisture in discrete quantities of material.

THE SUMMARY OF THE INVENTION

In accordance with the present invention, a signal indicative of the water weight in a given sample of material and a signal indicative of the material weight in the same sample are used to calculate the percent moisture in the material sample. A source of microwave radiation is directed through a sample container transparent to the radiation and detected by a microwave receiver providing a measurement of attenuated microwave energy. The sample container is enclosed in an anechoic chamber along with the microwave transmitter and receiver to minimize inaccuracies due to reflected or re-emitted radiation. The sample container is retained on a device for weighing the material and providing an indication of that weight. A temperature sensor is also located within the sample cell to enable an accurate measure of the temperature of the sample material. The output microwave signal, temperature signal, and the signal indicating the weight of the sample material are then combined to calculate the percent moisture of the material and the bulk density.

It is therefore a feature of the present invention to provide a means for rapidly and accurately measuring the percent moisture of a sample.

It is a further feature of the invention to provide a microwave apparatus and technique for providing a measure of moisture of a specific volumetric quantity of sample material.

Yet another feature of the invention is to provide a determination of percent moisture wherein a weighing device is used to measure the weight of sample material and microwave energy is used to measure the weight of water contained in the sample.

Still a further feature of the invention is to provide a microwave moisture measuring apparatus and technique wherein the sample is retained in an anechoic chamber along with the microwave transmitting and receiving devices for reducing unwanted and stray reflections and emissions of microwave energy.

Still another feature of the invention is to provide a microwave moisture measuring apparatus and technique which allows a determination of bulk density of the sample material.

Yet another feature of the invention is to provide a microwave moisture measuring apparatus and technique which includes temperature compensation.

These and other novel features of the present invention will become apparent from the following detailed description when taken in connection with the accompanying drawings wherein:

BRIEF DESCRIPTION OF THE DRAWING

The FIGURE is a schematic diagram of the microwave moisture measuring apparatus in accordance with the present invention.

DETAILED DESCRIPTION OF A PREFERRED EMBODIMENT

Referring now to the FIGURE, a microwave moisture measuring apparatus is generally shown at 10 and includes a sample cell 11 for retaining a predetermined volume of moisture containing material 12. The cell 11 and the sample material 12 are retained within a chamber 13 designed to be an anechoic chamber which prevents unwanted reflections and emissions of microwave radiation within the chamber. A microwave transmitting antenna 14 is located within the chamber 13 on one side of the cell 11 and positioned to direct microwave radiation through the cell 11 at power levels and frequencies which are substantially constant over a given measurement period. Likewise, a microwave receiving antenna 15 is positioned within the chamber 13 on the opposite side of cell 11 to receive microwave radiation which is transmitted through the sample material 12. The cell 11 may be constructed of any well known material which is transparent to microwave radiation at the frequencies employed and is configured in any manner which enables the unobstructed passing of that microwave energy through the sample material 12. The sample cell should be constructed to contain a volume between 200 and 1000 cubic centimeters. The walls of the sample cell should be less than 5 millimeters thick, so they do not interfere with the passage of microwave energy through the sample 12.

The anechoic chamber is likewise constructed in any conventional manner and of those materials necessary to produce the appropriate properties of an anechoic chamber. Such properties are well known and will not be further described, it being understood that the interior of such a chamber is lined with microwave energy absorbing material intended to absorb microwave energy impinging against all sides of the chamber to prevent reflection or re-emission of such waves into the chamber. Any construction or configuration which is capable of defining such a chamber is acceptable for purposes of the present invention so long as the materials and configuration reduce to the greatest extent possible the reception of unwanted radiation in receiver 15 which would reduce the accuracy of measurement of the transmitted signal from 14.

A weighing device 16 is also positioned and located within the chamber 13 and affixed to receive the sample cell 11 thereon to provide an indication of the weight of the sample material 12. A temperature sensor 17 is likewise located within the chamber 13 and attached to the cell 11 to provide a measurement of the temperature of the material 12 within that sample volume. The weighing device may comprise any conventional scale or other device capable of providing an output from 16 which is an accurate measurement of the weight of the material 12 retained within sample cell 11. The temperature sensor should be chosen for a quick response, on the order of 20 seconds or less. Several methods of temperature sensing which meet this requirement are available commercially, and the specific structures forming these devices are not critical as long as they provide an accurate reading of temperature in the desired time span.

Microwave radiation is generated in a conventional microwave generator 18, capable of providing 10 to 100 milliwatts of microwave energy. The microwave energy passes through an isolator 19, which is a device which prevents microwave reflection from traveling back to the generator 18. From the isolator 19, microwave energy passes through a level set attenuator 20 and is coupled to microwave transmit antenna 14. Again, the construction of the microwave generator 18 and components 19, 20 and 14 is conventional, and numerous devices are commercially available to fulfill this purpose. In the moisture measuring process, microwave frequencies in the spectrum between 2 GHz and 25 GHz may be employed, and the microwave devices selected should be chosen for the specific frequency chosen. The present apparatus described may use 10.525 GHz as the moisture measuring frequency, but special applications may dictate use of a higher or lower frequency.

The transmitting antenna 14 may take the shape of a microwave horn or other structure capable of directing the microwaves through the transparent cell 11 and thus the material 12 to the receiving antenna 15. The antenna 15 is likewise of conventional construction and may be a typical microwave horn positioned on the opposite side of cell 11 to receive the microwave energy from transmitting antenna 14 and provide an output of that received energy to a detector 1, which rectifies the microwave energy into a usable signal.

The detector output 21 and the outputs from the weighing device 16 and temperature sensor 17 are provided through lines 22, 24, and 23 respectively, to the computing unit 25. The output of the computing device 25, the operation of which will be subsequently described, is then constructed to provide a calculation and indication of percent moisture by a display 26 and an indication of bulk density by a display 7. The elements 26 and 27 can be digital meters which provide a readout directly indicating the percent moisture and bulk density as computed by unit 25.

Broadly, the unit 25 is designed to receive a signal 2 indicative of the attenuation of the microwave energy and thus the weight of the water in sample 12. The unit 25 also receives an indication of the weight of the material 2 through line 24 and a signal indicative of sample temperature through line 23. Unit 25 may modify the signal received from 23 in accordance with a predetermined scale to provide a signal capable of modifying the computed value for water weight. As can be seen, once a value for the weight of the sample is obtained and a value for the weight of water in the sample is obtained (as modified by the temperature signal), the calculation of percent moisture can be made by dividing the modified water weight by the sample weight. The unit 25 makes this calculation and provides an output through meter 26. Alternatively, the temperature signal from 23 could be used in the computing unit 25 to modify the percent moisture calculation (obtained by dividing water weight by sample weight) subsequent to the calculation, but prior to the output to the display 26. Additionally, the volume of the sample cell 11, which is constant, can be entered into unit 25 and the bulk density of sample 12 calculated by dividing the weight of sample 12 by the volume to produce an output on meter 27 indicating bulk density.

The unit 25 may be constructed from any conventional structures capable of making the calculations required above. By way of example, the unit 25 may be a conventional digital computer having analog inputs from lines 22, 23, and 24, as well as an input (not shown) representing the sample cell volume. The analog inputs may be appropriately modified by analog to digital converters to provide digital representations of the values received. The computer 25 may then calculate the percent moisture and bulk density for outputs to meters 26 and 27 by way of direct digital readout. Alternatively, the output signals could be converted by digital to analog converters and displayed on known meter devices.

In operation, a sample material 12 is first inserted into sample cell 11 to provide a sample of predetermined volumetric quantity. Microwave radiation, generated at frequencies which are optimally absorbed by water molecules, is provided to antenna 14 so that it is directed through material 12. In accordance with the present invention, the microwave energy is generated at levels of about 10 to 100 milliwatts. This level of radiation allows transmission through material 12 in the sample cell 11, but does not cause any measurable heating of the material 12 which might cause the evaporation of volatiles or otherwise change the nature of the sample 12 to be analyzed. The receiving antenna 15 detects the attenuated microwave energy from transmitting antenna 14 and provides that signal to the unit 25. At the same time, the sensor 17 and weighing device 16 provide their outputs to the unit 25 as previously described. Naturally, the weighing device 16 can be calibrated to compensate for the weight of cell 11 so that the output 24 is a direct measure of the weight of sample 12. Once the above outputs have been provided to unit 25, the above described computations are made so that direct readings of percent moisture and bulk density can be made from unit 25, thereby providing an accurate and continuous measure of those parameters for the material 12. Naturally, by simultaneously supplying the signals from outputs 22, 23 and 24 to the computing unit 25, a real time readout of the present moisture is obtained.

The moisture analysis based on evaporative techniques uses a sample size of about 5 grams. With such a small quantity of material, it is difficult to obtain a representative sample of the material to be analyzed. The continuous on-line methods described in U.S. Pat. Nos. 4,131,845 and 3,499,499 are designed for rather large quantities of material and are not suitable for discrete sample analysis. The sample size in the above described apparatus and technique lies between these two extremes, and is generally expected to be between 100 and 1000 grams. This sample size is more representative of the average properties of the material to be analyzed, and yet the sample is small enough to be practical for discrete sample analysis. There is no necessity for sample preparation by grinding or other methods, so long as the sample material is substantially uniform for filling the sample volume. This increases the speed of processing the material for moisture analysis as well as the accuracy of the readings. Analysis of discrete samples is thus permitted without long delays for drying times and inaccuracies due to factors caused by heating the product. Further, by performing the microwave measurement within the anechoic chamber, inaccuracies due to unwanted reflections and emissions are avoided. The above use of anechoic chamber, water weight measurement, sample weight measurement and temperature compensation to produce a percent moisture display provides an apparatus of improved speed and accuracy with less complex components. This allows the device to be used with a greater variety of materials and processes than otherwise attainable due to the prohibitive costs, complexities and inaccuracies of prior art devices. These are all advantages that are not taught by the prior art.

While the invention has been described with reference to particular structural elements, it is apparent that other equivalent structures could be used which are capable of performing the disclosed functions in accordance with the inventive teachings. Obviously, many other modifications are possible in light of the above teaching. It is therefore to be understood that within the scope of the appended claims, the invention may be practiced otherwise than as specifically described.

I claim:

1. An apparatus for analyzing a sample of moisture containing material comprising:
    first means for forming a chamber effectively preventing reflection of microwave energy;
    second means defining a sample cell space for retaining a moisture containing sample material, said second means being arranged to be disposed in said chamber;
    third means for transmitting microwave energy through said second means in said chamber;
    fourth means for receiving radiation transmitted through said space and providing a first output signal representative of water weight in a sample material therein;
    fifth means coupled to said first and second means for providing a second output signal representing the weight of a sample material including the water weight retained in said space;
    sixth means for receiving said first and second output signals and providing a third output signal representing the percent by weight moisture content of material retained in said space; and
    seventh means for measuring the temperature of the sample material retained in said space during weight sensing operation and providing a fourth output signal.

2. The apparatus of claim 1 further including: eighth means for modifying said third output signal representing percent moisture with said fourth output signal to produce a corrected third output signal representing percent by weight moisture of a sample material in said space.

3. The apparatus of claim 1 wherein said means forming the chamber is lined with microwave absorbent material.

4. The apparatus of claim 1 wherein said means for forming a volume forms a volume sufficient to retain weight of sample material in the range of 100 grams to 1000 grams.

5. The apparatus of claim 1 wherein said first means formed of a material substantially transparent to microwave radiation.

6. The apparatus of claim 5 wherein said second means transmits microwave radiation in the range of GHz to 30 GHz.

7. The apparatus of claim 1 wherein said second means transmits microwave energy at a level of 10 milliwatts to 100 milliwatts.

8. The apparatus of claim 1 further including:
means for providing a signal representing the volume of said space; and
means coupled to receive said signal representing volume and said second output signal for providing a fifth output signal representing bulk density of a sample material.

9. The apparatus of claim 1 further including indicator means coupled to receive said third output signal representing percent moisture for displaying that output.

10. The apparatus of claim 1 wherein said means forming said chamber is constructed of a material substantially absorbent of microwave energy at the transmitted frequencies.

11. The apparatus of claim 1 wherein the means for measuring the temperature of the sample material comprises a temperature sensor coupled to sense the temperature of the sample material in said chamber.

12. The apparatus of claim 1 wherein said dividing means further includes means for providing a signal corresponding to the volume of the sample, and means for dividing the signal representing said volume into the output signal representing said water weight to produce an output signal representing bulk density of a sample material.

13. The apparatus of claim 12 further including ninth means defining an indicator coupled to receive the output signals representing percent moisture and bulk density for displaying those outputs.

14. An apparatus for analyzing a sample of moisture containing material comprising:
a source of microwave energy of predetermined frequencies;
transmitter means coupled to said source for transmitting said microwave energy;
wall means forming a chamber effectively preventing reflection of microwave energy;
sample cell means removably positioned in said chamber in the path of said transmitted microwave energy for retaining a sample of moisture containing material in the path of said microwave energy such that said transmitted microwave energy is attenuated by moisture in said sample in said path, said sample cell means being substantially transparent to microwave energy at said predetermined frequencies;
receiver means positioned to receive microwave energy transmitted through said chamber by said transmitter means and providing an output representing the microwave energy transmitted through said sample cell means;
means coupled to said receiver means for providing a signal corresponding to the output signal representing the weight of the sample material retained therein;
weighing means coupled to weigh said sample cell means and a sample material retained therein for providing an output signal representing the weight of the sample material retained therein;
temperature sensing means coupled to said sample cell means for detecting the temperature of the sample material retained in said sample cell means during the transmission of microwave energy therethrough;
output means coupled to simultaneously receive said output signals representing water weight, sample weight and sample material temperature for calculating and providing an output signal representing percent by weight moisture of a sample material; and
anechoic chamber means enclosing each of said transmitter means, receiver means and sample cell means within a chamber constructed and designed to absorb microwave radiation at said predetermined frequencies to reduce microwave reflections and emissions within said chamber.

15. The apparatus of claim 14 wherein said source produces microwave frequencies in the range of 2 GHz to 30 GHz.

16. The apparatus of claim 15 wherein said transmitter means transmits microwave energy in the range of 10 milliwatts to 100 milliwatts.

17. The apparatus of claim 16 wherein said sample cell means is constructed to retain a volume of material having a weight in the range of 100 grams to 1000 grams.

18. The apparatus of claim 14 wherein said source is constructed to provide microwave energy at frequencies in the range absorbed by water.

* * * * *